(12) United States Patent
Baldauf et al.

(10) Patent No.: US 10,251,708 B2
(45) Date of Patent: *Apr. 9, 2019

(54) INTRAVASCULAR CATHETER FOR MODELING BLOOD VESSELS

(71) Applicant: International Business Machines Corporation, Armonk, NY (US)

(72) Inventors: Julia S. Baldauf, South Melbourne (AU); Darcy J. Beurle, Melbourne (AU); Matthew Downton, Carlton (AU); Kerry Halupka, Melbourne (AU); Stephen M. Moore, Melbourne (AU); Christine Schieber, Southbank (AU)

(73) Assignee: International Business Machines Corporation, Armonk, NY (US)

( * ) Notice: Subject to any disclaimer, the term of this patent is extended or adjusted under 35 U.S.C. 154(b) by 28 days.

This patent is subject to a terminal disclaimer.

(21) Appl. No.: 15/498,159

(22) Filed: Apr. 26, 2017

(65) Prior Publication Data

US 2018/0310992 A1 Nov. 1, 2018

(51) Int. Cl.
*A61B 34/20* (2016.01)
*A61B 34/10* (2016.01)

(52) U.S. Cl.
CPC .............. *A61B 34/10* (2016.02); *A61B 34/20* (2016.02); *A61B 2034/101* (2016.02)

(58) Field of Classification Search
None
See application file for complete search history.

(56) References Cited

U.S. PATENT DOCUMENTS

| 6,275,724 | B1 | 8/2001 | Dickinson et al. | |
|---|---|---|---|---|
| 6,813,512 | B2 | 11/2004 | Aldefeld et al. | |
| 8,849,375 | B2 | 9/2014 | Baumgart | |
| 2007/0268287 | A1* | 11/2007 | Magnin | A61B 5/0062 345/419 |
| 2008/0260231 | A1* | 10/2008 | Weese | A61B 6/481 382/132 |
| 2010/0030061 | A1* | 2/2010 | Canfield | A61B 6/541 600/413 |
| 2010/0201786 | A1* | 8/2010 | Schaefer | G06T 7/30 348/47 |
| 2012/0035437 | A1 | 2/2012 | Ferren et al. | |
| 2014/0005530 | A1 | 1/2014 | Liu et al. | |

(Continued)

OTHER PUBLICATIONS

Bourantas, et al., A method for 3D reconstruction of coronary arteries using biplane angiography and intravascular ultrasound images. Computerized Medical Imaging and Graphics, vol. 29, issue 8, Nov. 2005, pp. 597-606.

(Continued)

*Primary Examiner* — Vikkram Bali
(74) *Attorney, Agent, or Firm* — Grant Johnson; Otterstedt, Ellenbogen & Kammer, LLP

(57) ABSTRACT

A method of generating a 4D model includes capturing imagery of a catheter and a vessel as the catheter is directed through the vessel to a location of interest, wherein the catheter is disposed on a guidewire, constructing a 3D time varying reference curve describing a trajectory of the guidewire, and constructing a time varying 3D model of the artery using the reference curve.

7 Claims, 6 Drawing Sheets

(56) References Cited

U.S. PATENT DOCUMENTS

2015/0282777 A1    10/2015   Compas et al.
2016/0073854 A1    3/2016   Zeien

OTHER PUBLICATIONS

Athanasiou et al., Three-dimensional reconstruction of coronary arteries and plaque morphology using CT angiography—comparison and registration with IVUS, BMC Medical Imaging, Jan. 2016, pp. 1-13.

Bourantas, et al., A new methodology for accurate 3-dimensional coronary artery reconstruction using routine intravascular ultrasound and angiographic data: implications for widespread assessment of endothelial shear stress in humans. EuroIntervention, vol. 9, issue 5, Apr. 2013, pp. 582-593.

Doulaverakis, et al., IVUSAngio tool: a publicly available software for fast and accurate 3D reconstruction of coronary arteries. Computers in biology and medicine, vol. 43, issue 11, Nov. 2013, pp. 1793-1803.

Prause et al., Towards a geometrically correct 3-D reconstruction of tortuous coronary arteries based on biplane angiography and intravascular ultrasound. The International Journal of Cardiac Imaging, vol. 13, issue 6, May 1997, pp. 451-462.

Ge et al., Rotation-induced evolution of far-field emission patterns of deformed microdisk cavities, Optica, Mar. 2015, pp. 1-6.

Anonymous, Light-powered gyroscope is world's smallest: Promises a powerful spin on navigation, http://www.nanowerk.com/nanotechnology-news/newsid=39634.php, Apr. 2015, pp. 1-5.

Julia S. Baldauf et al., unpublished U.S. Appl. No. 15/857,738, filed Dec. 29, 2017, Intravascular Catheter for Modeling Blood Vessels, pp. 1-23 plus 6 sheets of drawings.

Paul J. Otterstedt, List of IBM Patents or Patent Applications Treated as Related, Jun. 25, 2018, pp. 1-2.

\* cited by examiner

ABSTRACT# INTRAVASCULAR CATHETER FOR MODELING BLOOD VESSELS

BACKGROUND

The present disclosure relates generally to an intravascular catheter and to a method for using an intravascular catheter for modeling the geometry of blood vessels.

Cardiovascular Disease is a leading health problem in the developed world, with Coronary Artery Disease (CAD) being a particularly important problem. CAD typically occurs when part of the smooth, elastic lining inside a coronary artery becomes hardened, stiffened, and swollen with plaque. Plaque typically consists of calcium deposits, fatty deposits, and abnormal inflammatory cells. The formation of a plaque is termed Atherosclerosis. This plaque can cause an obstruction to the supply of oxygenated blood to the heart muscle and can cause chest pain (angina), and ultimately lead to heart attack and death.

The field of Interventional Cardiology is a branch of cardiology that deals specifically with catheter based treatments of structural heart diseases such as CAD. During a procedure known as Percutaneous Coronary Intervention (PCI) a catheter is inserted into a major systemic artery in either the groin or the arm and guided towards the entrance to the coronary tree. This catheter takes the form of a thin tube, through which a radio-opaque dye may be delivered into the bloodstream, allowing for visualization of the coronary arteries using a special type of X-ray imaging called Fluoroscopy.

If the vessel narrowing is deemed severe enough, a common treatment is the insertion of a stent to increase the diameter of the artery. To place the stent, another catheter is threaded through the blood vessels via a guidewire into the heart where the coronary artery is narrowed by plaque. When the catheter is in place, a balloon tip covered with a stent is inflated. The balloon tip compresses the plaque and expands the stent. Once the plaque is compressed and the stent is in place, the balloon is deflated and withdrawn with the catheter. The stent stays in the artery, holding the artery open. If the stent is not aligned correctly with the walls of the artery, termed incomplete stent apposition (ISA), there is an increased risk of long term negative outcomes such as myocardial infarction and stent thrombosis.

One of the challenges in this field is accurately assessing the state of disease in a patient's coronary arteries. Coronary angiograms are commonly used by clinicians to manually identify and quantify the degree of a stenosis, wherever they may appear. Given an angiogram's finite resolution, the fact that they are 2D projections of a complex three-dimensional (3D) structure, and the fact that a stenosis can reduce the amount of contrast agent flowing through a stenosis, reducing its visibility, has meant that in many cases other catheter based imaging techniques are used. These techniques include Intravascular Ultrasound (IVUS) or Intravascular Optical Coherence Tomography (OCT), that acquire images of an artery and stenosis from the interior of the artery using an imaging sensor located at the catheter tip. Although these modalities provide much higher resolution images of the interior of an artery, they do not acquire any information about the 3D position and orientation of the catheter tip while the images are being acquired (e.g., if an OCT dataset is acquired while retracting the imaging sensor through a tortuous curved arterial branch, this could not be ascertained by examining the images).

BRIEF SUMMARY

According to an embodiment of the present invention, a method of generating a 4-Dimensional model includes capturing imagery of a catheter and a vessel as the catheter is directed through the vessel to a location of interest, wherein the catheter is disposed on a guidewire, constructing a 3-Dimensional time varying reference curve describing a trajectory of the guidewire, and constructing a time varying 3-Dimensional model of the artery using the reference curve.

According to an exemplary embodiment of the present invention, a method of generating a four-dimensional (4D) model during a Percutaneous Coronary Intervention (PCI) procedure comprises capturing imagery of a catheter and a vessel as the catheter is directed through the vessel to a location of interest, wherein the catheter is disposed on a guidewire and comprises a plurality of markers and a monitoring body, and wherein the imagery is captured from at least two different viewpoints, segmenting the guidewire and the at least one marker from the imagery and back projecting a segmented guidewire and at least one segmented marker into a three-dimensional (3D) space to define a time varying reference curve defining a motion of the monitoring body, recording accelerometer and gyroscope data of the catheter using a combination of sensors as the catheter is pulled away from the location of interest, integrating the accelerometer and gyroscope data in time, predicting a linear and a rotational position of the monitoring body in the imagery, and constructing the 4D model of the monitoring body and the vessel using the predicted linear and rotational position of the monitoring body, wherein the 4D model includes a time varying surface describing the vessel.

According to an embodiment of the present invention, a catheter includes a monitoring body and a pair of markers disposed on the monitoring body, each marker of the pair of markers encircling the monitoring body, wherein the pair of markers are configured to indicate, through their appearance from a given point of view, an orientation of the monitoring body.

According to an embodiment of the present invention, a catheter includes an outer sheath, an inner sheath disposed within the outer sheath, a guidewire, a monitoring body disposed within the inner sheath, an imaging sensor disposed at a distal end of the monitoring body, and a pair of radio-opaque elliptical hoops disposed on the monitoring body, each radio-opaque elliptical hoop of the pair of radio-opaque elliptical hoops encircling the monitoring body, wherein the pair of radio-opaque elliptical hoops are configured to indicate, through their appearance in a two-dimensional projection, an orientation of the monitoring body.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments may provide one or more of the following advantages:

Provide accurate visualization of the morphology of a patient's coronary arteries, combining both the 3D time varying nature of the arteries, with a high resolution view of the arterial wall and its composition.

Allow for high resolution patient specific computer simulation of hemodynamics through a stenosis or a deployed stent, to assess ISA and disruption to normal blood flow and provide a means for predicting restenosis.

Enable personalized stent design and deployment, reducing the risk of ISA and thereby improving outcomes for patients.

These and other features and advantages of the present invention will become apparent from the following detailed description of illustrative embodiments thereof, which is to be read in connection with the accompanying drawings.

BRIEF DESCRIPTION OF THE SEVERAL VIEWS OF THE DRAWINGS

Preferred embodiments of the present invention will be described below in more detail, with reference to the accompanying drawings.

DETAILED DESCRIPTION

According to an embodiment of the present invention, a catheter is configured to record an orientation of its tip as it moves through a coronary artery. According to an embodiment of the present invention, a direction vector is defined for the tip of the catheter and optionally, a measure of twist of the catheter. According to an embodiment of the present invention, this information is combined with imaging modalities such as Intravascular Ultrasound (IVUS) and intravascular Optical Coherence Tomography (OCT), enabling a reconstruction of the arterial lumen. According to an embodiment of the present invention, a technique for determining the 3D position and orientation of an imaging catheter during a pullback provides technical advantages including enabling the details of the arterial wall and its composition to be positioned correctly.

Figure 1:
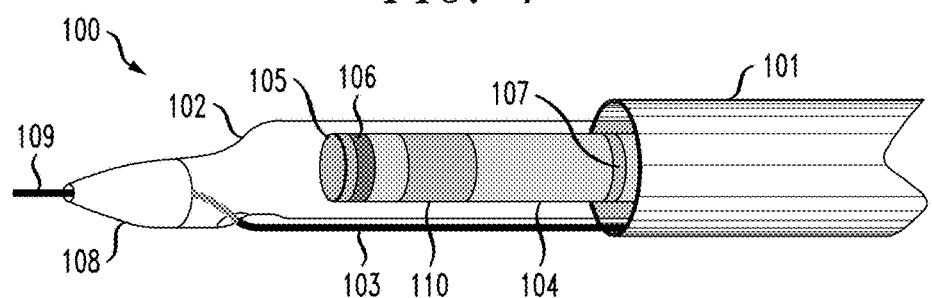
FIG. 1 is a diagram of a catheter according to an embodiment of the present invention.
Figure 2A:
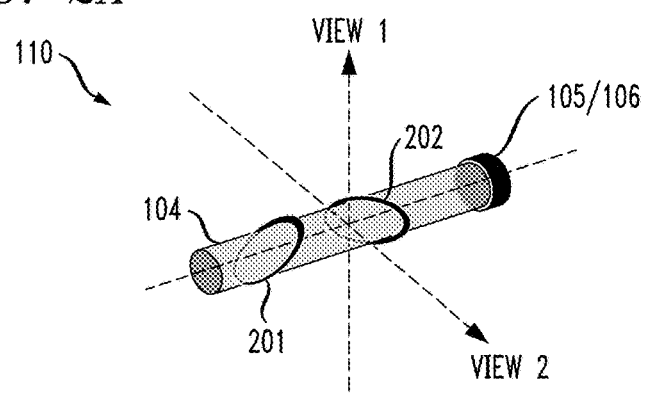
FIGS. 2A-C are perspective views of a geometric array of radio-opaque markers according to an embodiment of the present invention.
Figure 2B:
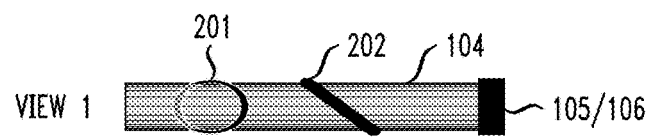
Figure 2C:
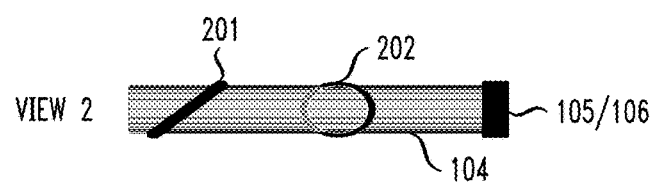

FIG. 1 is a diagram of a catheter 100 according to an embodiment of the present invention, wherein the catheter 100 comprises an outer sheath 101, an inner sheath 102 a guidewire 103, a monitoring body 104, a sensor 105 (e.g., an imaging sensor) attached to the monitoring body 104, a first marker 106 (e.g., a lens marker), a second or proximal marker 107, a distal tip marker 108 and a distal tip 109 of the guidewire 103. The catheter 100 further comprises a geometric array 110, described herein.

The catheter 100 is configured for acquiring IVUS or OCT images, wherein the outer sheath 101 remains in place during a pullback of the inner sheath 102, guidewire 103 and monitoring body 104, including the sensor 105, through the coronary artery (not shown). Furthermore, the markers 106-108 and 110 can be observed in an angiogram.

According to an embodiment of the present invention, the geometric array 110 includes radio-opaque markers 201-202. The radio-opaque markers 201-202 can be retro-fitted onto existing catheters to indicate twist of the catheter. These radio-opaque markers 201-202 are arranged in a fashion that enables determination of the orientation of the monitoring body 104. The radio-opaque markers 201-202 include 2 elliptical hoops (201 and 202, respectively) affixed to the exterior of the monitoring body, such that they remain stationary with respect to the imaging modality (OCT, or IVUS) The radio-opaque markers 201-202 are disposed orthogonal to one another, and at a fixed distance from the markers 106-108. Since the entirety of each loop is radio-opaque, a full ellipse is visible in the angiogram (or other imaging method) from all angles, unless that angle is parallel to the plane of the ellipse, in which case a single line is seen in the angiogram. Each orientation of the catheter from a particular viewpoint is associated via a lookup table with a unique 2D projection. Therefore, given a particular marker 2D projection seen on the angiogram, the pattern of the markers in relation to the angle of view of the angiogram relates to a single angle of twist of the catheter tip.

Figure 3:
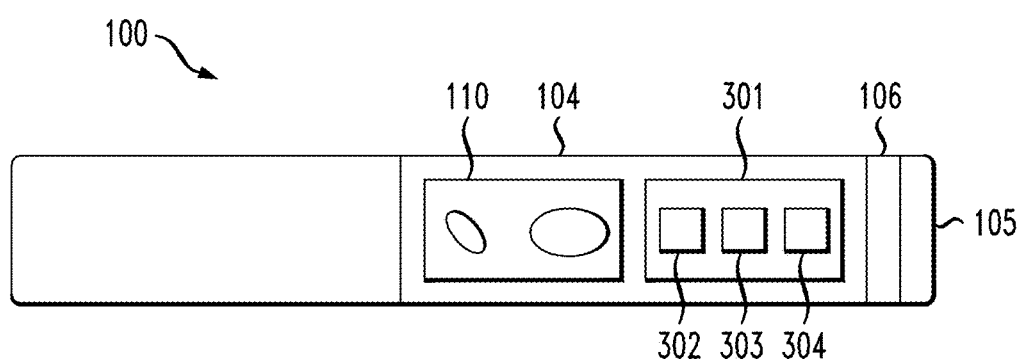
FIG. 3 is a block diagram of a catheter according to an embodiment of the present invention.

In addition to the geometric array 110, according to an embodiment of the present invention, the catheter 100 includes an Inertial Measurement Unit (IMU) configured to record orientation data relative to a datum point. The IMU provides linear and rotational information about the catheter, enabling the determination of a trajectory, which can be periodically confirmed in the angiogram via the orientation of the markers. FIG. 3 shows the monitoring body 104 of the catheter 100 including the geometric array 110, which is positioned on the device alongside the IMU 301. The IMU 301 includes one or more of a gyroscope 302 (such as an optical gyroscope), an accelerometer 303, and a magnetometer 304, positioned on the monitoring body, at the catheter tip. According to an embodiment of the present invention, 3 orthogonal accelerometers and 3 orthogonal gyroscopes are included in the IMU in order to measure inertial acceleration and rotation position, respectively, in 3 dimensions. The sensors 302-304 can be placed in any combination possible alongside the sensor 105 and first marker 106. It should be appreciated that other configurations of sensors are contemplated, and that these configurations would be understood a person of ordinary skill in the art in view of the present disclosure.

Figure 4:
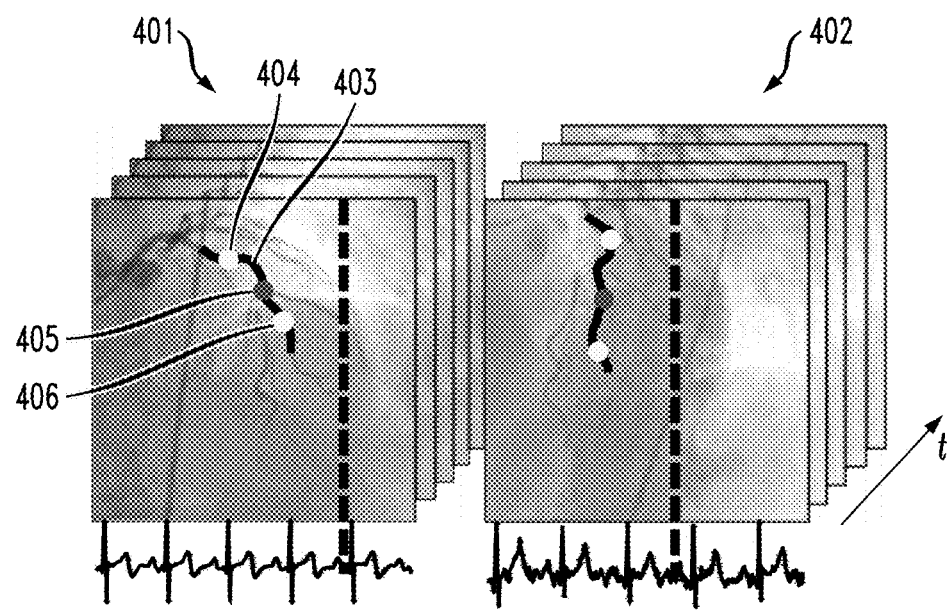
FIG. 4 is a view of two sets of angiograms acquired from different viewpoints according to an embodiment of the present invention.
Figure 5:
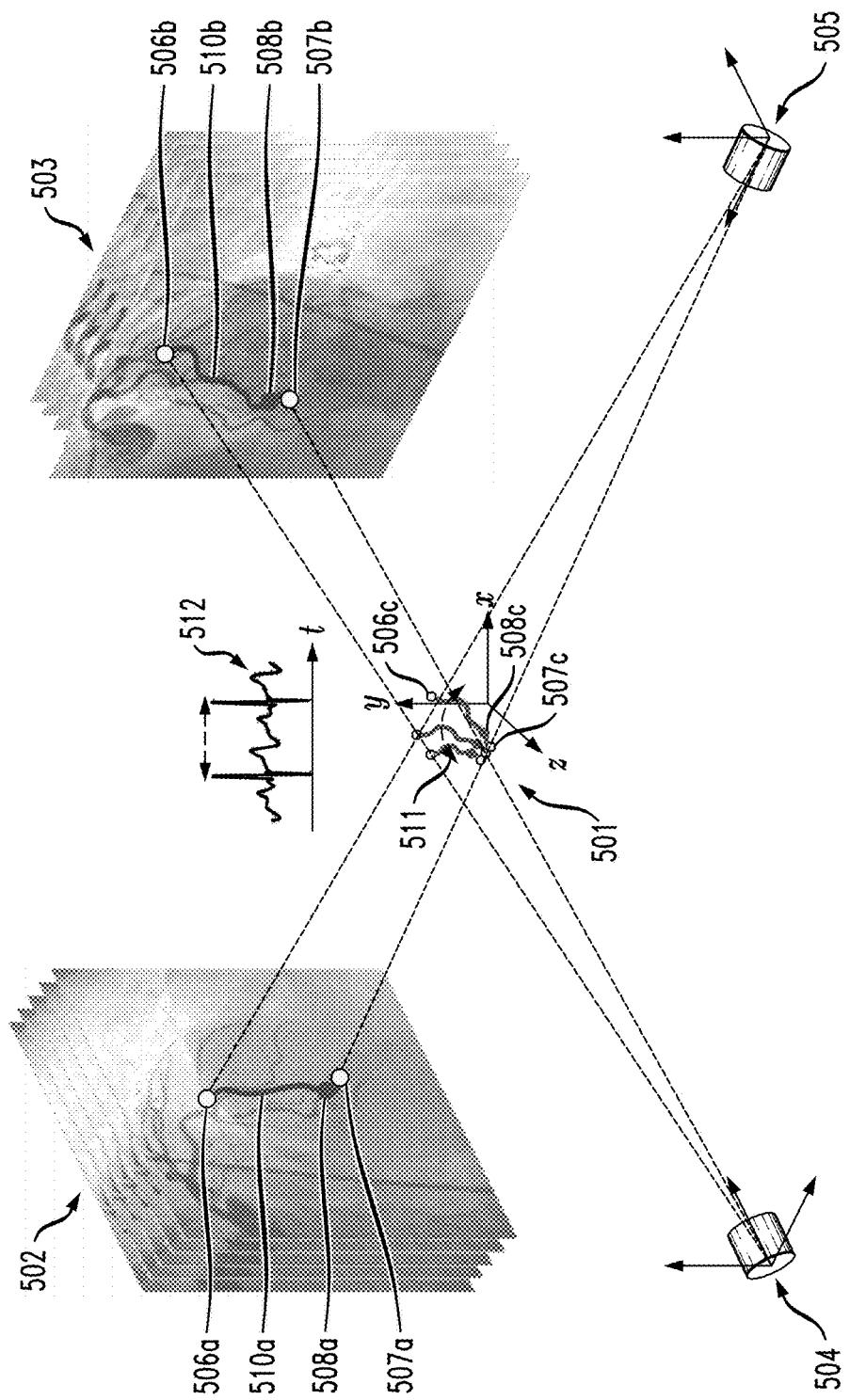
FIG. 5 is an illustration of a guidewire and markers segmented for defining a 4D trajectory according to an embodiment of the present invention.

According to an embodiment of the present invention, a method 800 (see FIG. 8) of generating a four-dimensional (4D) model during a PCI procedure includes threading a catheter (incorporating an imaging sensor, IMU, and specialized markers) onto a guidewire and directing the catheter through a coronary artery to a location of interest (e.g., stenosis or otherwise) 801. According to an embodiment of the present invention, the method includes capturing imagery (e.g., angiograms) 802 from two different viewpoints simultaneously using bi-plane angiography over a single cardiac cycle. According to an embodiment of the present invention, the method includes capturing imagery (e.g., angiograms) 802 from two different viewpoints, one at a time (using single plane angiography to view from two viewpoints over different cycles) (401-402), for at least one cardiac cycle as illustrated in FIGS. 4-5. In the case of a scanner without bi-lane imaging capabilities, a first angiogram is acquired using a scanner, a gantry supporting the scanner is rotated changing the view point, and a second angiogram acquired using the scanner. According to an embodiment of the present invention, the guidewire 403 and the markers, e.g., 404, (including the markers 106-108 and geometric array 110) are visible in the imagery.

According to an embodiment of the present invention, the method further comprises processing the imagery 803. More particularly, using these two angiograms 401-402, the guidewire 403 and markers 404 are segmented in each frame and projected into 3D space to define a time varying reference curve defining the motion of the monitoring body, which is affixed to the catheter, as a sequence of coordinates in space and time (i.e., a 4D trajectory) (see FIG. 5). In addition, the rotational position of the imaging sensor, relative to the angiogram viewpoint, can be determined through observation of a marker pattern of the geometric array 110 in each angiogram frame, wherein both the initial linear and rotational positions of the imaging sensor can be defined and specified as an initial condition.

According to an embodiment of the present invention, the segmentation can include extracting a coronary artery tree from each of a sequence of angiogram images, creating a mean artery tree from the extracted coronary artery trees, and projecting the mean artery tree back onto each of the sequence of angiogram images to recover a complete coronary artery tree for each of the sequence of angiogram images. Here, the disclosure of U.S. patent application Ser. No. 14/243,106, entitled Detecting Coronary Stenosis Through Spatio-Temporal Tracking, and filed on Apr. 2, 2014, is incorporated by reference in its entirety. It should be understood that other methods of segmenting the guidewire and markers can be used, for example, rule based classification of pixels of the frames and deep learning/neutral network classifiers can be used in one or more embodiments of the present invention.

FIG. 5 is an illustration of the definition of the time varying 3D reference curve 501. Using two angiogram runs (502, 503) acquired from different perspectives (504, 505) the proximal marker (e.g., 506*a-b*) and distal tip markers (e.g., 507*a-b*), the lens marker (e.g., 508*a-b*), and guidewire (e.g., 510*a-b*) can be segmented and triangulated into the global world coordinate system (i.e., the one in an x,y,z coordinate system). The time varying 3D reference curve 501 includes the location (over the cardiac system indicated by arrow 511) of the proximal marker 506*c*, the distal top marker 507*c*, the lens marker 508*c* and the guidewire 510*c*. Curve 512 illustrates an ECG trace (available for each run), which is used to map angiogram frames to corresponding positions in the cardiac cycle (where it is assumed that the coronary geometry would be in the same physical position in the world coordinate system). The different perspectives correspond to imaging devices (e.g., an X-Ray source) used to acquire the runs.

According to an embodiment of the present invention, the processing 803 can be performed using existing techniques. In one example, the guidewire 403, proximal marker 404, lens marker 405 and distal marker 406 are extracted from each of a sequence of angiogram images of angiograms 401-402 by estimating a position of the guidewire 403 and markers 404-406 from each of the sequence of angiogram images. Mean positions of the guidewire 403 and markers 404-406 are calculated and re-aligned back to each of the sequences of angiogram images. This results in a set of positions widths along a common set of artery segments that can be compared over time.

The method further includes recording accelerometer and gyroscope data using some combination of sensors 302-304 as the catheter is wound back 804. This data includes a measure of inertial acceleration and rotational position in 3 dimensions. By integrating the accelerometer and gyroscope data in time based on the initial condition 804, a predicted linear and rotational position of the imaging sensor is estimated 805, to where the acquired frame can be located (see FIG. 6). More particularly, according to an embodiment of the present invention, the pullback has constant rate while the sensor 105 acquires images at a specified frame rate.

Figure 6:
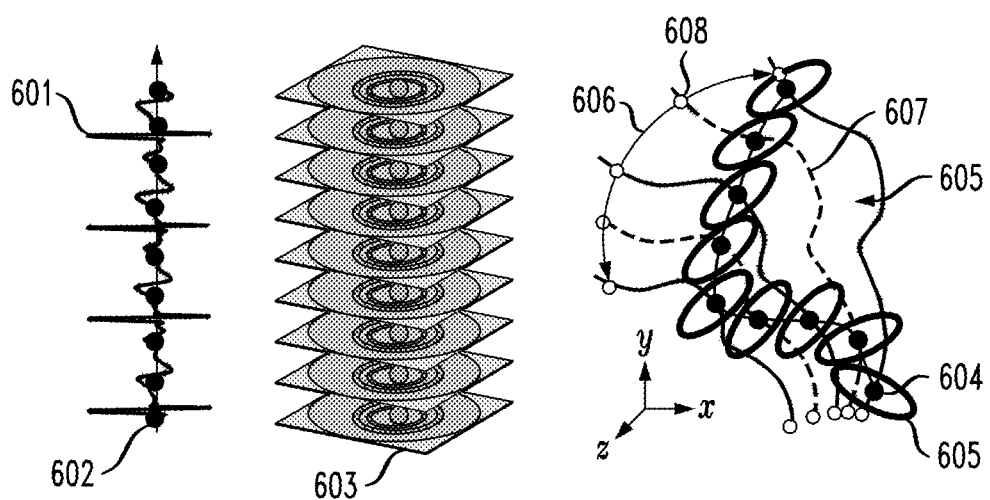
FIG. 6 is an illustration of a pullback procedure according to an embodiment of the present invention.

FIG. 6 is an illustration of the pullback procedure and the mapping of arterial cross sections obtained from the intravascular images, onto the reference curve. More particularly FIG. 6 illustrates a heart rhythm recording 601 with indications, e.g., 602, corresponding to each frame of the dataset, e.g., 603. The heart rhythm recording 601 illustrates the ECG trace acquired with the angiogram during the pullback and the indications, e.g., 602, depict the positions in the multiple cardiac cycles over which images of the pullback procedure are acquired. Similarly, indication 602 corresponds to marker 604 in the mapping. In the mapping, the rotation position of the image sensor is illustrated by the ovals, e.g., 605, which correspond to the markers contained therein. The ovals, e.g., 605, and markers, e.g., 604, illustrate the arterial wall cross section and centroid respectively, segmented from each image, e.g., 603, during the pullback, which are subsequently mapped to positions along the reference curve, defining a time varying geometry. Time-varying anatomy (e.g., changing shape of the artery during the cardiac cycle) is indicated by arrow 606. The curves (e.g., 607) and markers (e.g., 608) illustrate the guidewire and the time varying position of the proximal and distal markers (see for example, FIG. 5, markers 506, 507), respectively.

According to an embodiment of the present invention, the method includes correcting for the drift error 806 accumulated in the accelerometer recording, using magnetometer data. According to an embodiment of the present invention, a filtering approach using the predicted and observed positions of the monitoring body is applied. By making use of the fact that the imaging sensor is constrained to move along the guidewire, the initial position and the known pullback rate are used to compute a location along the reference curve at the moment in time that the frame was acquired. Since the moment in time will not likely coincide with a point in time at which the reference curve is defined, the position is interpolated between neighboring points in space and time on the reference curve. At this stage a filtered estimate of the linear and angular position of the imaging sensor is determined and the data can be locked on to that point on the reference curve and oriented such that the image normal vector is parallel to the reference curve tangent at that point. While the image frames acquired by OCT or IVUS show the vessel cross-section of each frame location at a single point in the cardiac cycle, it is assumed that the cross-section at that vessel location does not change throughout the cycle, and remains stationary in relation to the associated point on the reference curve.

Figure 8:
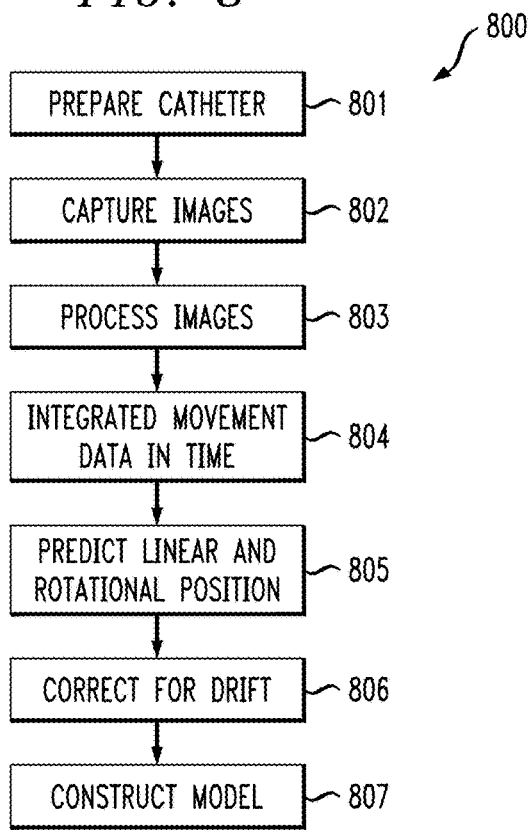
FIG. 8 is a block diagram of a method of building a 4D model according to an embodiment of the present invention.

At this point the data acquisition is complete and the model is constructed 807. According to an exemplary embodiment of the present invention, the model is built by applying known segmentation techniques to extract contours from each frame defining the arterial wall and stent, applying or generating of point cloud data that may be used to define a time varying surface describing the arterial wall. The outcome of the method depicted in FIG. 8 is a model defining the 4 dimensional structure of the blood vessel in question, including the cross-section along the curve, and movement of the vessel throughout the cardiac cycle.

Figure 7:
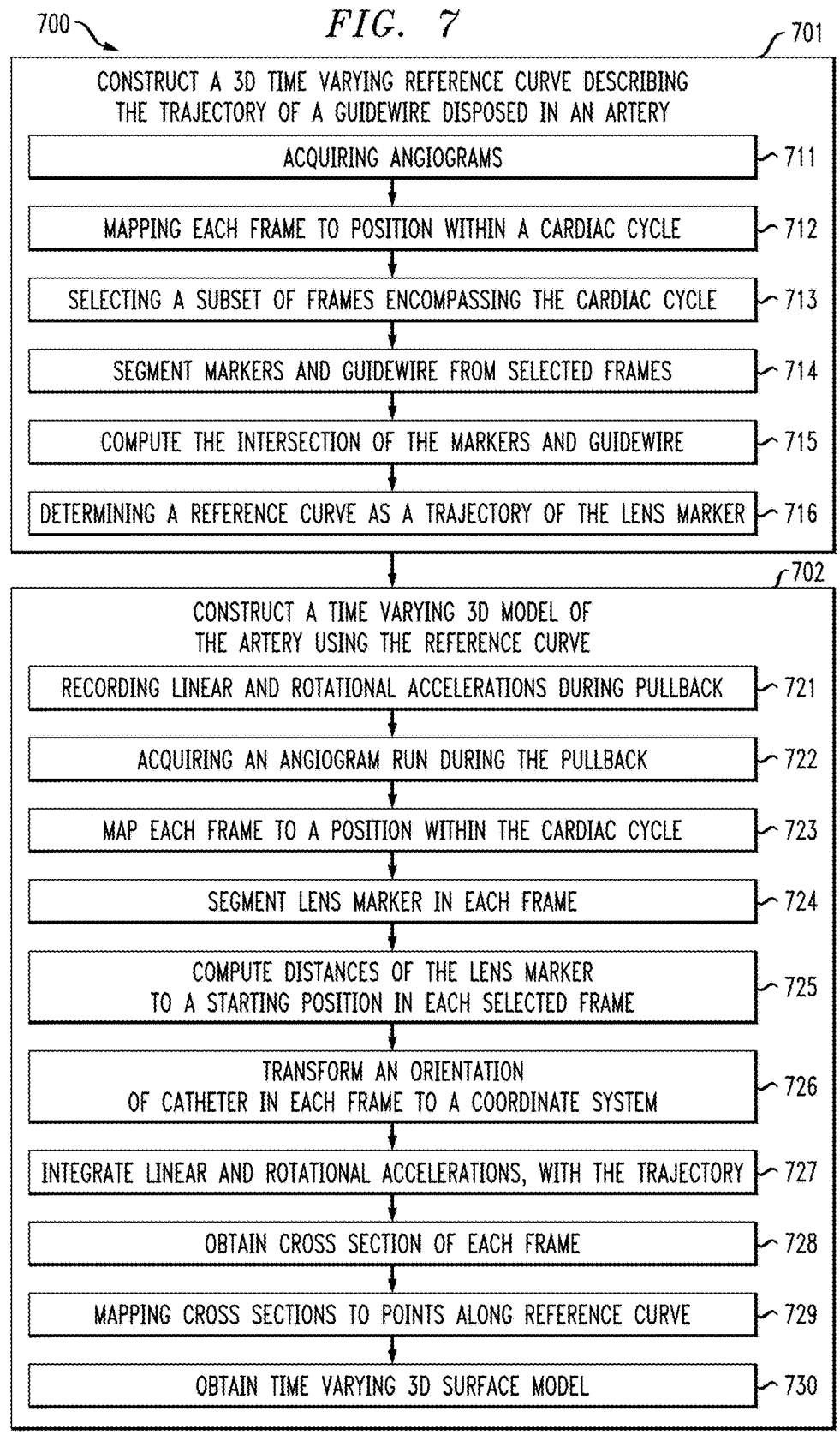
FIG. 7 is a block diagram of a method of building a 4D model according to an embodiment of the present invention.

Consider the following exemplary implementation illustrated in the method 700 of FIG. 7; according to one or more embodiments of the present invention, with a patient lying supine in X-Ray imaging system and a guidewire navigated through a branch/stenosis of interest, such as in as Percutaneous Coronary Intervention procedure, a 3D time varying reference curve describing the trajectory of the guidewire disposed in an artery is constructed at 701, and a high-resolution time varying 3D computer model of the artery is constructed at 702.

According to an exemplary embodiment of the present invention, the construction of the 3D time varying reference curve describing the trajectory of the guidewire 701 uses image segmentation to extract pixels describing the guidewire from each angiogram, and performs a mapping to a world coordinate system to output the time varying 3D reference curve. According to an exemplary embodiment of the present invention, the time varying 3D reference curve is the trajectory of the guidewire. The trajectory of the guidewire is used to constrain calculations about the movement of the imaging sensor (and/or other components of the catheter) during pullback.

According to an exemplary embodiment of the present invention, as the 3D time varying reference curve describing the trajectory of the guidewire is built 701, an initial position and orientation of the lens marker is defined using image segmentation to extract pixels describing the elliptical markers, which are then mapped to the world coordinate system. The method uses at least two different angiograms taken from different viewpoints, to reconstruct the 3D world position of the elliptical markers. According to one or more embodiments of the present invention, it is assumed that the catheter and guidewire move in a periodic motion over time, where the motion of the guidewire from the first to the second scan corresponds with the motion of the heart. According to an exemplary embodiment of the present invention, when performing the pullback in the context of a non-bi-plane scanner, only one angiogram is acquired and used to track the lens marker. It should be understood that a bi-plane scanner can be used during pullback, and may provide additional imaging information. Given the 3D time varying reference curve, an image segmentation is performed on the angiogram(s) acquired during the pullback, and the position of the imaging sensor is mapped the onto the 3D time varying reference curve 702. According to an embodiment of the present invention, a lookup table is used for determining the orientation of the sensor based on the segmentation of the elliptical markers, where the lookup table includes data about known imagery of the elliptical markers corresponding to different orientations of the sensor.

According to an exemplary embodiment of the present invention, and with reference to FIG. 7, the construction of the 3D time varying reference curve describing the trajectory of the guidewire 701 comprises acquiring at least two angiogram runs from different viewing angles 711 (e.g., greater than 25 degrees apart, either with a monoplane or biplane X-Ray imaging system) with the guidewire, and the proximal marker, the distal tip marker, and the lens marker visible over a complete cardiac cycle (e.g., with no dye injected), mapping each frame to positions within the cardiac cycle (e.g., using well-known signal processing techniques to locate the QRS complex seen on a typical electrocardiogram) using the ECG data embedded in the runs as metadata 712 and selecting a subset of frames from each run that encompass at least one complete cardiac cycle 713, applying image/video processing analytics to the selected frames from each run to segment the markers and guidewire (e.g., using a method such as Convolutional Neural Networks (CNN) trained to perform object detection on the markers and semantic pixel labeling on the guidewire) 714, using the well-known imaging parameters embedded in the runs as metadata (e.g. primary (left and right anterior oblique views, LAO and RAO, respectively) and secondary (caudal and cranial view, CRAN and CAUD, respectively) viewing angles, distance from source to intensifier (SID) and source to isocenter (SOD), pixel spacing) compute the intersection of the marker points and points along the guidewire in the isocenter world coordinate system (e.g., using triangulation) over time 715, in determining the trajectory of the lens marker in the world coordinate system as a function of time 716.

According to an exemplary embodiment of the present invention, the construction of the high-resolution time varying 3D computer model of the artery 702 comprises performing an intravascular imaging pullback at a user specified and controlled rate during which time IMU linear and rotational accelerations are recorded 721, acquiring, during the pullback, at least one angiogram run from one of the viewing angles used to build the reference curve in 701, such that the lens marker is visible 722 (e.g., with no dye injected), using the ECG data embedded in the run as metadata to map each frame to a position within the cardiac cycle 723, applying image/video processing analytics to segment the lens marker in each frame (e.g., using a CNN trained to perform semantic pixel labeling on the lens marker such that the appearance of the elliptical markers can be observed) 724, using a known pullback rate (and given the fact that the imaging sensor is constrained to move along the guidewire), compute distance of lens marker along reference curve relative to starting position (e.g., a start of the pullback, a start of the recording, etc.), at each step during pullback 725, and using observed appearance of elliptical markers, compute orientation of catheter in imaging frame of reference and transform this to the world coordinate system 726. At this point there are a set of observed positions and orientations from each angiogram frame acquired during the pullback. The method further comprises using the world coordinate position of the lens marker at the time the pullback began to integrate the linear and rotational accelerations forward in time, to integrate this modeled trajectory with the observed trajectory obtained from the angiogram run and reference curve (e.g., using a Kalman filter) 727. The method further comprises applying image processing analytics to each frame of the intravascular pullback (e.g. using a CNN, or level set method to extract the arterial wall, stent, etc) to obtain cross sectional curves 728, mapping each extracted cross section to the corresponding point along the reference curve and connect them (e.g., by defining triangles between sets of points on adjacent cross sections) 729 to obtain the time varying 3D surface model 730.

According to an exemplary embodiment of the present invention, the lens marker 106 is one of the elliptical markers 201-202. In a case where the lens marker 106 is a ring shaped marker as shown in FIG. 1, separate analytics can be used to track the ring shaped lens marker 106 and the elliptical markers 201-202. In at least one exemplary embodiment of the present invention, the ring shaped lens marker 106 is omitted. Because the imaging sensor, lens marker 106 (if present) and elliptical markers 201-202 are rigidly connected, tracking the elliptical markers 201-202 can yield sufficient tracking information, without separately tracking the lens marker 106.

Recapitulation:

According to an embodiment of the present invention, a method of generating a 4-Dimensional model includes capturing imagery of a catheter and a vessel as the catheter is directed through the vessel to a location of interest, wherein the catheter is disposed on a guidewire, constructing a 3-Dimensional time varying reference curve describing a trajectory of the guidewire, and constructing a time varying 3-Dimensional model of the artery using the reference curve.

Medical images typically adhere to the Digital Imaging and Communications in Medicine (DICOM) format once they are transferred from an imaging system that acquires them to a database system (e.g., Picture Archiving and Communication System (PACS)). At this point, metadata regarding medical images (e.g., angiogram RAO-LAO, SID, pixel spacing, etc., or OCT pixel spacing, etc.) can be embedded in appropriate DICOM header fields. According to an embodiment of the present invention, rotational information about a catheter is encoded in medical images. According to at least one embodiment of the present invention, the IMU acceleration and IVUS/OCT imaging data are intercepted (e.g., from the imaging system) and a model is generated before outputting data (e.g., the IMU acceleration and IVUS/OCT imaging data) to the PACS in DICOM format. According to an embodiment of the present invention, the rotational information about a catheter is used in building a 3D model of an artery. According to an embodiment of the present invention, the model so built improves the accuracy of computer simulations of hemodynamics (e.g. virtual FFR), leads to improved visualizations of stent placement (improving outcomes for patients), allows for wall shear stress to be determined on a patient specific basis (stenosis form in areas of low shear stress) as a possible predictor of restenosis, and enables personalized stent design and deployment.

According to an embodiment of the present invention, an accelerometer and a gyroscope are disposed at the tip of the catheter, near a laser marking system 105. The rotational position of the catheter is recorded and matched to the position of the laser. Integration of this information allows for a complete trajectory of the laser tip to be determined.

According to an embodiment of the present invention, a catheter having an accelerometer and a gyroscope enables improved visualization of complex stenotic geometry, side branches, stents, and allow for the generation of high resolution 3D computer models of vascular geometries that could be used for computer simulations of blood flow, wall shear stress, generation of personalized stent designs, of stent placement, and once deployed, assessment of their impact on normal haemodynamics.

Embodiments of the present invention utilize high-resolution imaging modalities such as IVUS and intravascular OCT, and is able to determine spatial position and orientation as the catheter steered through the cardiovascular system, building a 4D (i.e., 3D+time varying) representation of the coronary geometry.

Embodiments of the present invention utilize IVUS imaging modality to assess the composition of plaque, thereby informing the treatment plan, and providing information regarding vessel wall and plaque thickness to the 4D model.

According to an embodiment of the present invention, a method of generating a four-dimensional (4D) model during a Percutaneous Coronary Intervention (PCI) procedure includes capturing imagery of a catheter and a vessel 802 as the catheter is directed through the vessel to a location of interest, wherein the catheter is disposed on a guidewire and comprises a plurality of markers and a monitoring body, and wherein the imagery is captured from at least two different viewpoints, segmenting the guidewire and the at least one marker from the imagery and back projecting a segmented guidewire and at least one segmented marker into a three-dimensional (3D) space to define a time varying reference curve defining a motion of the monitoring body 803, recording accelerometer and gyroscope data of the catheter using a combination of sensors as the catheter is pulled away from the location of interest 803, integrating the accelerometer and gyroscope data in time 804, predicting a linear and a rotational position of the monitoring body in the imagery 805, and constructing the 4D model of the monitoring body and the vessel using the predicted linear and rotational position of the monitoring body, wherein the 4D model includes a time varying surface describing the vessel 807.

According to an exemplary embodiment of the present invention, the trajectory of the guidewire is used to determine the position of the lens marker and imaging sensor. Embodiments of the present invention overcome a problem in the art where an imaging system (e.g., X-ray imaging system), a catheter imaging system and an IMU are not synchronized to provide measurements at the same points in time. Embodiments of the present invention facilitate the positioning of images along a reference curve at correct times, at the times that the images were acquired. Exemplary embodiments of the present invention integrate acceleration data forward in time to predict a trajectory of the lens marker and imaging sensor, with periodic corrections to these predictions given an angiogram frame where the position is actually observed.

The methodologies of embodiments of the disclosure may be particularly well-suited for use in an electronic device or alternative system. Accordingly, embodiments of the present invention may take the form of an entirely hardware embodiment or an embodiment combining software and hardware aspects that may all generally be referred to herein as a "processor," "circuit," "module" or "system."

Furthermore, it should be noted that any of the methods described herein can include an additional step of providing a computer system for generating a 4D model during a PCI procedure. Further, a computer program product can include a tangible computer-readable recordable storage medium with code adapted to be executed to carry out one or more method steps described herein, including the provision of the system with the distinct software modules.

Figure 9:
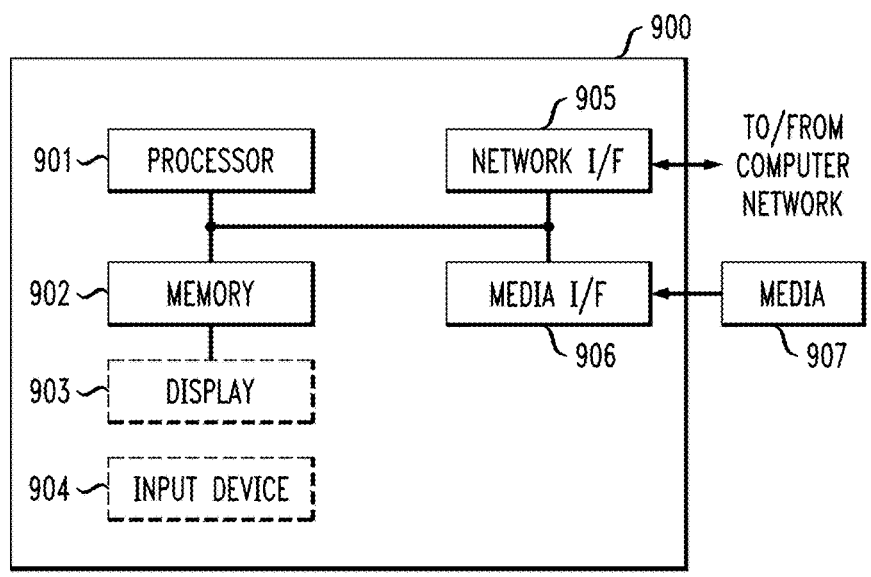
FIG. 9 is a block diagram depicting an exemplary computer system embodying a method for modeling a blood vessel according to an exemplary embodiment of the present invention.

Referring to FIG. 9; FIG. 9 is a block diagram depicting an exemplary computer system embodying the computer system for generating a 4D model during a PCI procedure according to an embodiment of the present invention. The computer system shown in FIG. 9 includes a processor 901, memory 902, display 903, input device 904 (e.g., keyboard), a network interface (I/F) 905, a media I/F 906, and media 907, such as a signal source, e.g., camera, Hard Drive (HD), external memory device, etc.

In different applications, some of the components shown in FIG. 9 can be omitted. The whole system shown in FIG. 9 is controlled by computer readable instructions, which are generally stored in the media 907. The software can be downloaded from a network (not shown in the figures), stored in the media 907. Alternatively, software downloaded from a network can be loaded into the memory 902 and executed by the processor 901 so as to complete the function determined by the software.

The processor 901 may be configured to perform one or more methodologies described in the present disclosure, illustrative embodiments of which are shown in the above figures and described herein. Embodiments of the present invention can be implemented as a routine that is stored in memory 902 and executed by the processor 901 to process the signal from the media 907. As such, the computer system is a general-purpose computer system that becomes a specific purpose computer system when executing routines of the present disclosure.

Although the computer system described in FIG. 9 can support methods according to the present disclosure, this system is only one example of a computer system. Those skilled of the art should understand that other computer system designs can be used to implement embodiments of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A non-transitory computer readable medium comprising computer executable instructions which when executed by a computer cause the computer to perform a method of generating a four-dimensional (4D) model during a Percutaneous Coronary Intervention (PCI) procedure, said method comprising:
   capturing imagery of a catheter and a vessel as the catheter is directed through the vessel to a location of interest, wherein the catheter is disposed on a guidewire and comprises a plurality of markers and a monitoring body, and wherein the imagery is captured from at least two different viewpoints;
   segmenting the guidewire and at least one marker from the imagery and back projecting a segmented guidewire and at least one segmented marker into a three-dimensional (3D) space to define a time varying reference curve defining a motion of the monitoring body;
   recording accelerometer and gyroscope data of the catheter using a combination of sensors as the catheter is pulled away from the location of interest;
   integrating the accelerometer and gyroscope data in time;
   predicting a linear and a rotational position of the monitoring body in the imagery; and
   constructing the 4D model of the monitoring body and the vessel using the predicted linear and rotational position of the monitoring body, wherein the 4D model includes a time varying surface describing the vessel.

2. The computer readable medium of claim 1, wherein capturing imagery comprises capturing a plurality of angiograms.

3. The computer readable medium of claim 1, wherein capturing imagery comprises capturing the different viewpoints simultaneously over a single cardiac cycle.

4. The computer readable medium of claim 1, wherein capturing imagery comprises capturing the different viewpoints one at a time over consecutive cardiac cycles.

5. The computer readable medium of claim 1, wherein the time varying reference curve defines the motion of the monitoring body as a sequence of coordinates in space and time.

6. The computer readable medium of claim 1, wherein the accelerometer and gyroscope data comprises a measure of inertial acceleration and rotational position in three dimensions.

7. The computer readable medium of claim 1, further comprising correcting for a drift error accumulated in the accelerometer data using magnetometer data.

* * * * *